United States Patent [19]

Zipperer et al.

[11] Patent Number: 5,192,767
[45] Date of Patent: Mar. 9, 1993

[54] 3-SUBSTITUTED PYRIDINES AND FUNGICIDES CONTAINING THEM

[75] Inventors: Bernhard Zipperer; Norbert Goetz, Worms; Ernst Buschmann, Ludwigshafen; Linhard Sproesser, Bad Duerkheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 617,374

[22] Filed: Nov. 26, 1990

Related U.S. Application Data

[63] Continuation of Ser. No. 257,278, Oct. 19, 1988, abandoned.

[30] Foreign Application Priority Data

Oct. 14, 1987 [DE] Fed. Rep. of Germany ....... 3734750

[51] Int. Cl.$^5$ ..................... A61K 31/44; C07D 213; C07D 28; C07D 213; C07D 55; C07D 213; C07D 57
[52] U.S. Cl. .................................. 514/277; 514/357; 546/330; 546/334; 546/335; 546/344
[58] Field of Search ............... 546/344, 330, 334, 335; 514/277, 357

[56] References Cited

U.S. PATENT DOCUMENTS

| | | | |
|---|---|---|---|
| 3,335,148 | 8/1967 | Krumkalns | 546/269 |
| 3,361,753 | 1/1968 | Krumkalns | 546/274 |
| 3,397,273 | 8/1968 | Van Heyninglen et al. | 514/277 |
| 4,710,508 | 12/1987 | Bergmeier et al. | 514/357 |

FOREIGN PATENT DOCUMENTS

| | | | |
|---|---|---|---|
| 0117485 | 9/1984 | European Pat. Off. | 544/335 |
| 214566 | 3/1987 | European Pat. Off. | 546/344 |
| 243940 | 11/1987 | European Pat. Off. | 548/572 |
| 244739 | 11/1987 | European Pat. Off. | 548/570 |

OTHER PUBLICATIONS

Chem. Abstracts, vol. 73(21), Abst. No. 109,645-x, Nov. 23, 1970.
Chem. Abstracts, vol. 102(7) Abst. No. 62089-u, Feb. 18, 1985.

*Primary Examiner*—Alan L. Rotman
*Attorney, Agent, or Firm*—Oblon, Spivak, McClelland, Maier & Neustadt

[57] ABSTRACT

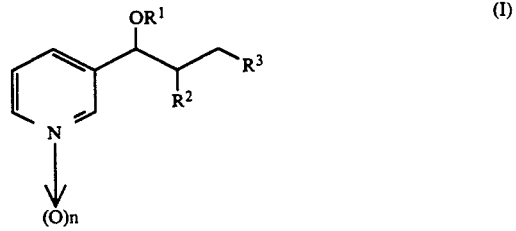

where
$R^1$ is hydrogen, alkyl, alkenyl, alkynyl, acyl, haloacyl, benzoyl or benzyl;
$R^2$ is hydrogen, alkyl, cycloalkyl, cycloalkylalkyl, alkylcycloalkyl, arylalkyl or aryloxyalkyl,
$R^3$ is the radical

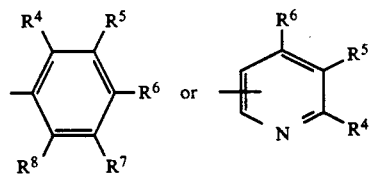

$R^4$ to $R^8$ being identical or different and each denoting hydrogen, alkyl, alkoxy, haloalkyl, alkoxycarbonyl, dialkylamino, phenyl, hydroxy or halogen, and $R^4$ and $R^5$, or $R^6$ and $R^7$ together denote —CH=CH—CH=CH—, n is 0 or 1, salts thereof which are tolerated by plants, and fungicides containing these compounds.

7 Claims, No Drawings

3-SUBSTITUTED PYRIDINES AND FUNGICIDES CONTAINING THEM

This application is a continuation of application Ser. No. 07/257,278, filed on Oct. 13, 1988, now abandoned.

The present invention relates to novel 3-substituted pyridine derivatives and fungicides which contain these compounds, and methods for controlling fungi.

Structurally related 3-propenylpyridines, e.g. 2-n-butyl-3-(4-methylphenyl)-1-(3-pyridyl)-2-propen-1-ol, 2-n-butyl-3-(4-methylphenyl)-1-(3-pyridyl)-2-propen-1-one and 2-n-butyl-3-(4-fluorophenyl)-1-(3-pyridyl)-2-propen-1-ol are disclosed as fungicides in EP-214 566. However, their action is not always completely satisfactory for certain indications, particularly at low application rates.

We have found that 3-substituted pyridine derivatives of the formula

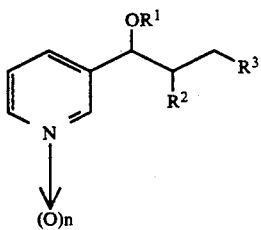

where $R^1$ is hydrogen, $C_1$–$C_8$-alkyl, $C_3$–$C_8$alkenyl, $C_3$–$C_8$-alkynyl, $C_2$–$C_{12}$-acyl, $C_2$–$C_{12}$-haloacyl or unsaturated $C_3$-acyl, or is benzoyl which is unsubstituted or monosubstituted to trisubstituted by $C_1$–$C_4$-alkyl, $C_1$–$C_4$-alkoxy, phenyl, acetoxy, $C_1$–$C_4$-haloalkyl, halogen or nitro, or is benzyl which is unsubstituted or substituted by 1 to 3 radicals of the type $C_1$–$C_4$-alkyl, $C_1$–$C_4$-alkoxy, $C_1$–$C_4$-haloalkyl, halogen, cyano or nitro, $R^2$ is hydrogen, $C_1$–$C_{12}$-alkyl, $C_3$–$C_{12}$-cycloalkyl, $C_4$–$C_{20}$-cycloalkylalkyl, $C_4$–$C_{20}$-alkylcycloalkyl, unsubstituted or substituted $C_7$–$C_{20}$-arylalkyl, or unsubstituted or substituted $C_7$–$C_{20}$-aryloxyalkyl whose aryl radicals are unsubstituted or monosubstituted to trisubstituted by $C_1$–$C_4$-alkyl, $C_1$–$C_4$-alkoxy, $C_1$–$C_4$-haloalkyl or halogen, $R^3$ is a radical

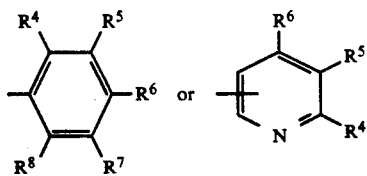

where $R^4$ to $R^8$ independently of one another are each hydrogen, $C_1$–$C_4$-alkyl, $C_1$–$C_4$-alkoxy, $C_1$–$C_4$-haloalkyl, $C_2$–$C_4$-alkoxycarbonyl, $C_2$–$C_4$-dialkylamino, phenyl, hydroxyl or halogen, and $R^4$ and $R^5$ or $R^5$ and $R^6$ together may furthermore be the group —CH═CH—CH═CH—, and n is 0 or 1, and their plant-tolerated salts surprisingly have a substantially better fungicidal action than the unsaturated pyridine derivatives disclosed in EP-214 566.

$R^1$ is, for example, hydrogen, methyl, ethyl, n-propyl, isopropyl, n-butyl, isobutyl, tert-butyl, n-pentyl, isopentyl, n-hexyl, neohexyl, n-heptyl, n-octyl, 2,4,4-trimethylpent-2-yl, 2-ethylhexyl, allyl, 2-methylallyl, 3-methylallyl, 3,3-dimethylallyl, 3-buten-1-yl, 3-octen-1-yl, propargyl, 3-octyl-1-yl, acetyl, mono-, di- or trichloroacetyl, trifluoracetyl, propionyl, 3-bromopropionyl, butyryl, 4-bromobutyryl, 3-methylbutyryl, 3,3-dimethylbutyryl, pentanoyl, hexanoyl, heptanoyl, octanoyl, 2-ethylhexanoyl, nonanoyl, decanoyl, lauroyl, dodecanoyl, acryloyl, benzoyl, mono-, di- or trimethylbenzoyl, 4-tert-butylbenzoyl, 4-phenylbenzoyl, fluorobenzoyl, mono-, di- or trichlorobenzoyl, trifluoromethylbenzoyl, mono-, di- or trimethoxybenzoyl, 2-acetoxybenzoyl, mono- or dinitrobenzoyl, benzyl, mono-, di- or trimethylbenzyl, 4-tert-butylbenzyl, mono-, di- or trimethoxybenzyl, trifluoromethylbenzyl, trichloromethylbenzyl, mono-, di- or trichlorobenzyl, cyanobenzyl or mono- or dinitrobenzyl.

$R^2$ is, for example, hydrogen, methyl, ethyl, n-propyl, isopropyl, n-butyl, isobutyl, tert-butyl, n-pentyl, isopentyl, neopentyl, n-hexyl, neohexyl, n-heptyl, n-octyl, n-nonyl, n-decyl, n-undecyl, n-dodecyl, cyclopentyl, cyclohexyl, cyclooctyl, cyclododecyl, 2-cyclohexylethyl, 3-cyclohexyl-2-methylpropyl, 4-tert-butylcyclohexyl, benzyl, mono-, di- or trimethylbenzyl, 4-tert-butylbenzyl, mono-, di- or trimethoxybenzyl, trifluoromethylbenzyl, mono-, di- or trichlorobenzyl, fluorobenzyl, phenylethyl, (4-fluorophenyl)-ethyl, (chlorophenyl)-ethyl, (2,4-dichlorophenyl)-ethyl, phenylpropyl, 4-tert-butylphenylpropyl, 3-phenyl-2-propyl, 3-(4-tert-butylphenyl)-2-propyl, 3-(chlorophenyl)-2-propyl, 3-(fluorophenyl)-2-propyl, 3-(2,4-dichlorophenyl)-2-propyl, phenoxymethyl, mono-, di- or trichlorophenoxymethyl, fluorophenoxymethyl, phenoxyethyl, mono-, di- or trichlorophenoxyethyl, fluorophenoxyethyl, phenoxypropyl, mono-, di- or trichlorphenoxypropyl, flurophenoxypropyl, phenoxybutyl, mono-, di- or trichlorophenoxybutyl, mono-, di- or trichlorophenoxybutyl or fluorophenoxybutyl.

$R^3$ is, for example, phenyl, mono-, di- or trimethylphenyl, ethylphenyl, 4-tert-butylphenyl, mono-, di- or trimethoxyphenyl, trifluoromethylphenyl, trichloromethylphenyl, N,N-dimethyl(ethyl)aminophenyl, methoxycarbonylphenyl, hydroxyphenyl, biphenyl, mono-, di- or trichlorophenyl, fluorophenyl, naphthyl, pyridyl, methylpyridyl, chloropyridyl, quinolyl or isoquinolyl.

Plant-tolerated salts are, for example, addition salts with inorganic mineral acids, such as hydrochlorides, hydrobromides, sulfates, phosphates or nitrates; salts with formic acid or with alkylcarboxylic acids, such as acetates, 2-ethylhexanoates or oxalates; and salts with arylsulfonic acids, such as benzenesulfonates, toluenesulfonates or dodecylbenzenesulfonates.

The compounds of the formula I may have two centers of asymmetry and therefore occur in two diastereomeric forms, which, if required, can be separated by known methods. The present invention relates to the individual diastereomers as well as their mixtures.

The compounds of the formula I may be in the form of the pyridines or in the form of the pyridine N-oxides.

The novel 3-substituted pyridines of the formula I can be prepared, for example, by reacting a pyridyl alcohol of the formula I

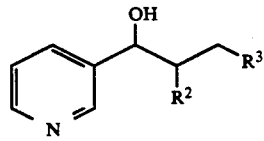

where $R^2$ and $R^3$ have the abovementioned meanings, with an alkyllating or acylating agent of the formula II $$R^1-X \qquad (II)$$

where $R^1$ has the abovementioned meanings, except for hydrogen, and X is a nucleofugic group, e.g. chlorine, bromine, iodine, methanesulfonate, benzenesulfonate or p-toluenesulfonate.

This reaction is advantageously carried out by a procedure in which a mixture of pyridyl alcohol of the formula I, not less than an equimolar amount of an auxiliary base and an inert, organic solvent, such as diethyl ether, tetrahydrofuran, dioxane, dimethylformamide, dimethyl sulfoxide, acetonitrile, toluene or xylene, is initially taken and the alkylating or acylating agent is metered in.

The reaction temperatures are from 0° to 120° C., preferably from 20° to 80° C.

Suitable auxiliary bases are inorganic and organic acid acceptors.

Examples of inorganic bases are sodium hydride, sodium amide, sodium hydroxide, sodium carbonate, potassium carbonate and potassium hydroxide.

Examples of organic bases are amines, in particular tertiary amines, such as triethylamine, ethyldiisopropylamine or pyridine, and alcoholates, such as sodium methylate, sodium ethylate or potassium tert-butylate.

In an advantageous variant of this process, the reactions of the pyridyl alcohols of the formula I with alkylating agents of the formula II are carried out in a two-phase system consisting of aqueous sodium hydroxide solution and an organic solvent, preferably toluene or dichlormethane, with the addition of a phase-transfer catalyst, e.g. tetra-n-butylammonium chloride, benzyltriethylammonium chloride or methyltrioctylammonium chloride.

The novel compounds I where $R^1$ is hydrogen are prepared, for example, by reducing a pyridyl ketone of the formula III or a pyridyl alcohol of the formula IV

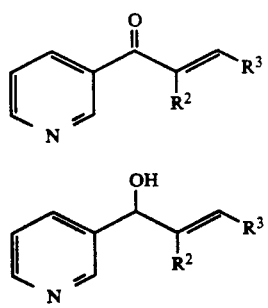

where $R^2$ and $R^3$ have the abovementioned meanings, with a reducing agent, for example a complex hydride or hydrogen, in the presence of a catalyst (cf. for example M. Hudlicky, Reductions in Organic Chemistry, page 119 et seq., Ellis Horwood Series, Chichester, 1984). The preparation of the pyridyl ketones of the formula III and of the pyridyl alcohols of the formula IV is known (EP-214 566).

In another process for the preparation of the novel compounds I where $R^1$ is hydrogen, for example, an organometallic compound of the formula V

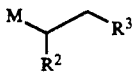

where $R^2$ and $R^3$ have the abovementioned meanings and M is lithium or the radical MgCl or MgBr, is reacted with nicotinaldehyde (3-formylpyridine). For this purpose, the organometallic compound of the formula V is advantageously initially taken in an inert solvent, preferably diethyl ether or tetrahydrofuran, and the nicotinaldehyde is metered in as a mixture with the same solvent at from −30° to +50° C.

The organometallic compounds of the formula V are obtainable from the corresponding halides (chlorides or bromides) by known processes (cf. for example Houben-Weyl, Methoden der Organischen Chemie, Volume 13/1, page 134 et seq., Georg Thieme Verlag, Stuttgart 1970; ibid., Volume 13/2a, page 54 et seq., George Thieme Verlag, Stuttgart, 1973). The latter are either known or can be prepared by known processes. The pyridine N-oxides are obtained from the pyridines by known processes, for example by oxidation with a peracid (cf. for example Katritzky and Lagowski, Chemistry of Heterocyclic N-Oxides, pages 21–56, Academic Press, New York, 1971).

The Examples which follow illustrate the preparation of the novel fungicidal pyridines.

EXAMPLE 1

2-n-butyl-3-(4-fluorophenyl)-1-(3-pyridyl)-propan-1-ol

In a 0.3 l stirred autoclave, a mixture of 17.1 g (0.6 mole) of 2-n-butyl-3-(4-fluorophenyl)-1-(3-pyridyl)-2-propan-1-ol, 160 ml of tetrahydrofuran and 4.5 g of a hydrogenation catalyst (0.5% of Pd on $Al_2O_3$) is hydrogenated at 30° C. and under a hydrogen pressure of 50 bar until the pressure remains constant. The solution is then filtered under suction over silica gel, the filtrate is evaporated down under reduced pressure and the residue is purified by distillation. Yield: 7.9 g of compound No. 1, bp. 187° C. (0.3 mbar).

EXAMPLE 2

2-n-butyl-3-(4-fluorophenyl)-1-(3-pyridyl)-propan-1-ol 2,4-dichlorobenzoate 4.6 g (0.022 mole) of 2,4-dichlorobenzoyl chloride, dissolved in 10 ml of dichloromethane, are added dropwise to a solution of 5.74 g (0.02 mole) of compound No. 1 in 50 ml of dichloromethane and 10 ml of triethylamine at room temperature. The mixture is stirred overnight, after which 30 ml of 10% strength $NaHCO_3$ solution are added and stirring is continued for a further hour. The organic phase is washed with water, dried over $MgSO_4$ and evaporated down under reduced pressure. The residue is purified by chromatography over silica gel using a 9:1 dichlormethane/acetone mixture as the mobile phase. 6.7 g (73% of theory) of compound No. 2 are obtained as a yellow oil.

EXAMPLE 3

2-n-butyl-3-(4-fluorophenyl)-1-(3-pyridyl)-propan-1-ol 4-chlorobenzyl ether 0.72 g (0.03 mole) of sodium hydride is added to a solution of 5.74 g (0.02 mole) of compound 1 in 20 ml of dimethylformamide, and the mixture is stirred at 50° C. until the evolution of hydrogen has ended. The mixture is cooled to room temperature, after which 4.0 g (0.025 mole) of 4-chlorobenzyl chloride in 10 ml of dimethylformamide are added dropwise sufficiently slowly to prevent the internal temperature from exceeding 40° C. Stirring is continued for 1 hour at room temperature (20° C.), 50 l of water are carefully added dropwise at 0° C. and 100 ml of ether are introduced. The aqueous phase is separated off and extracted by shaking with ether. The combined organic phases are dried over MgSO$_4$ and evaporated down under reduced pressure. The residue is purified by chromatography over silica gel using a 9:1 dichloromethane/acetone mixture as the mobile phase. 6.7 g (81% of theory) of compound No. 3 are obtained as a yellow oil.

EXAMPLE 4

3-(4-fluorophenyl)-1-(3-pyridyl)-propan-1-ol

A solution of 10.7 g (0.10 mole) of nicotinaldehyde in 100 ml of diethyl ether is added dropwise, while stirring, to a solution prepared from 2.92 g (0.12 mole) of magnesium and 24.4 g (0.12 mole) of 2-(4-fluorophenyl)-ethyl bromide in 250 ml of diethyl ether, and the mixture is then refluxed for 2 hours. Cooling is followed by hydrolysis with water, and the pH is brought to 8 with saturated aqueous NH$_4$Cl solution. The phases are separated, the aqueous phase is extracted twice more with ether, and the combined organic phases are washed with water and dried over NgSO$_4$. The solvent is evaporated off and the residue is distilled under reduced pressure to give 10.2 g (44% of theory) of compound No. 4 of boiling point 190° C. (2 mbar).

The following compounds are obtained in a corresponding manner.

TABLE 1

| Ex. no. | R$^1$ | R$^2$ | R$^3$ (n = 0) | bp/mp |
|---|---|---|---|---|
| 1 | H | n-butyl | 4-fluorophenyl | 187° C. (0.3 mbar) |
| 2 | 2,4-dichlorobenzoyl | n-butyl | 4-fluorophenyl | oil |
| 3 | 4-chlorobenzyl | n-butyl | 4-fluorophenyl | oil |
| 4 | H | H | 4-fluorophenyl | 190° (2 mbar) |
| 5 | H | n-butyl | 4-methylphenyl | 167° (0.1 mbar) |
| 6 | H | n-butyl | 4-tert.-butylphenyl | 197° C. (0.25 mbar) |
| 7 | H | n-butyl | 4-chlorophenyl | 196-200° C. (0.2 mbar) |
| 8 | H | n-butyl | 2,4-dichlorophenyl | |
| 9 | H | n-butyl | 4-methoxyphenyl | |
| 10 | H | n-butyl | 3-trifluoromethylphenyl | |
| 11 | H | n-butyl | 4-biphenyl | |
| 12 | H | n-butyl | 2-chlorophenyl | |
| 13 | H | n-butyl | 1-naphthyl | |
| 14 | H | n-butyl | 2-naphthyl | |
| 15 | H | n-butyl | 3-pyridinyl | |
| 16 | H | neo-pentyl | 4-fluorophenyl | |
| 17 | H | neo-pentyl | 4-chlorophenyl | |
| 18 | H | neo-pentyl | 2-chlorophenyl | |
| 19 | H | neo-pentyl | 2,4-dichlorophenyl | |
| 20 | H | n-heptyl | 2,4-dichlorophenyl | |
| 21 | H | n-heptyl | 2-chlorophenyl | |
| 22 | H | n-heptyl | 4-chlorophenyl | |
| 23 | H | n-heptyl | 4-fluorophenyl | |
| 24 | H | n-undecyl | 2,4-dichlorophenyl | |
| 25 | H | 2-fluorophenoxyethyl | 2,4-dichlorophenyl | |
| 26 | H | 2-fluorophenoxyethyl | 2-chlorophenyl | |
| 27 | H | 2-fluorophenoxyethyl | 4-chlorophenyl | |
| 28 | H | 2-fluorophenoxypropyl | 2,4-dichlorophenyl | |
| 29 | H | 2-fluorophenoxypropyl | 2-chlorophenyl | |
| 30 | H | 2-fluorophenoxypropyl | 4-chlorophenyl | |
| 31 | H | 4-fluorobenzyl | 4-chlorophenyl | |
| 32 | H | 4-fluorobenzyl | 2,4-dichlorophenyl | |
| 33 | H | 4-fluorobenzyl | 2-chlorophenyl | |
| 34 | H | 4-fluorobenzyl | 4-fluorophenyl | |
| 35 | H | 4-chlorobenzyl | 4-tert.-butylphenyl | |
| 36 | H | 4-chlorobenzyl | 2-chlorophenyl | |
| 37 | H | 4-chlorobenzyl | 2,4-dichlorophenyl | |
| 38 | acetyl | n-butyl | 4-fluorophenyl | |
| 39 | acetyl | n-butyl | 4-tert.-butylphenyl | |
| 40 | trifluoroacetyl | n-butyl | 4-tert.-butylphenyl | |
| 41 | H | H | 4-chlorophenyl | 200° C. (2 mbar) |
| 42 | H | H | 2-naphthyl | 230° (1 mbar) |
| 43 | H | CH$_3$ | phenyl | 170° (1 mbar) |
| 44 | H | H | 2-methylphenyl | 190° (2 mbar) |
| 60 | H | n-propyl | phenyl | |
| 61 | H | n-propyl | 4-chlorophenyl | |
| 62 | H | n-propyl | 2-chlorophenyl | |
| 63 | H | n-propyl | 2,4-dichlorophenyl | |
| 64 | H | n-propyl | 4-fluorophenyl | |
| 65 | H | n-propyl | 4-methylphenyl | |

TABLE 1-continued

| Ex. no. | R¹ | R² | n = 0 R³ | bp/mp |
|---|---|---|---|---|
| 66 | H | n-propyl | 4-tert.-butylphenyl | |
| 67 | H | iso-propyl | phenyl | |
| 68 | H | iso-propyl | 4-chlorophenyl | |
| 69 | H | iso-propyl | 2-chlorophenyl | |
| 70 | H | iso-propyl | 2,4-dichlorophenyl | |
| 71 | H | iso-propyl | 4-fluorophenyl | |
| 72 | H | iso-propyl | 4-tert.-butylphenyl | |
| 73 | H | ethyl | phenyl | |
| 74 | H | ethyl | 4-chlorophenyl | |
| 75 | H | ethyl | 2-chlorophenyl | |
| 76 | H | ethyl | 2,4-dichlorophenyl | |
| 77 | H | ethyl | 4-fluorophenyl | |
| 78 | H | ethyl | 4-tert.-butylphenyl | |
| 79 | H | ethyl | 4-methylphenyl | |
| 80 | H | methyl | 4-chlorophenyl | |
| 81 | H | methyl | 2-chlorophenyl | |
| 82 | H | methyl | 2,4-dichlorophenyl | |
| 83 | H | methyl | 4-fluorophenyl | |
| 84 | H | methyl | phenyl | |
| 85 | H | methyl | 4-tert.-butylphenyl | |
| 86 | H | methyl | 4-iso-propylphenyl | |
| 87 | H | methyl | 4-methoxyphenyl | |

TABLE 2

| Ex. no. | R¹ | R² | n = 1 R³ | bp/mp |
|---|---|---|---|---|
| 45 | H | n-butyl | 4-fluorophenyl | |
| 46 | H | n-butyl | 4-methylphenyl | |
| 47 | H | n-butyl | 4-tert.-butylphenyl | |
| 48 | H | n-butyl | 4-chlorophenyl | 128–130° C. |
| 49 | H | n-butyl | 2,4-dichlorophenyl | |
| 50 | H | n-butyl | 2-chlorophenyl | |
| 51 | H | n-butyl | 1-naphthyl | |
| 52 | H | neo-pentyl | 4-fluorophenyl | |
| 53 | H | neo-pentyl | 4-chlorophenyl | |
| 54 | H | n-heptyl | 4-fluorophenyl | |
| 55 | H | n-heptyl | 4-chlorophenyl | |
| 56 | H | n-heptyl | 2,4-dichlorophenyl | |
| 57 | H | n-undecyl | 4-fluorophenyl | |
| 58 | H | n-undecyl | 4-chlorophenyl | |
| 59 | H | n-undecyl | 2,4-dichlorophenyl | |
| 88 | H | n-propyl | 4-chlorophenyl | |
| 89 | H | n-propyl | 2,4-dichlorophenyl | |
| 90 | H | n-propyl | 2-chlorophenyl | |
| 91 | H | n-propyl | 4-fluorophenyl | |
| 92 | H | iso-propyl | 4-chlorophenyl | |
| 93 | H | iso-propyl | 2,4-dichlorophenyl | |
| 94 | H | iso-propyl | 2-chlorophenyl | |
| 95 | H | iso-propyl | 4-fluorophenyl | |
| 96 | H | ethyl | 4-chlorophenyl | |
| 97 | H | ethyl | 2,4-dichlorophenyl | |
| 98 | H | ethyl | 2-chlorophenyl | |
| 99 | H | ethyl | 4-fluorophenyl | |
| 100 | H | methyl | 4-chlorophenyl | |
| 101 | H | methyl | 2,4-dichlorophenyl | |
| 102 | H | methyl | 2-chlorophenyl | |
| 103 | H | methyl | 4-fluorophenyl | |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorbenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolines, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 5 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenezenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 6 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 5 is intimately mixed with 97 parts by weight of particulate kaolin. A dust is obtained containing 3% by weight of the active ingredient.

VII. 30 parts by weight of compound no. 6 is intimately mixed with a mixture consisting of 92 parts by weight of powdered silica gel and 8 parts by weight of paraffin oil which has ben sprayed onto the surface of this silica gel. A formulation of the active ingredient is obtained having good adherence.

VIII. 40 parts by weight of compound no. 1 is intimately mixed with 10 parts of the sodium salt of a phenosulfonic acid-urea-formaldehyde condensate, 2 parts of silica gel and 48 parts of water to give a stable aqueous dispersion. Dilution in water gives an aqueous dispersion.

IX. 20 parts by weight of compound no. 1 is intimately mixed with 2 parts by weight of the calcium salt of dodecylbenzenesulfonic acid, 8 parts by weight of a fatty alcohol polyglycol ether, 2 parts by weight of the sodium salt of a phenosulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore by mixed and applied together with fertilizers, Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;

nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone, 2-thiopyridine 1-oxide,
8-hydroxyquinoline and its copper salt,
2,3-dihydro-5-carboxanilido-6-methyl-1,4oxathiyne,
2,3-dihydro-5-carboxanilido-6-methyl-1,4oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino)-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-[3,5-dichlorophenyl]-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoxyimino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

The agents used for comparison purposes were
2-n-butyl-3-(4methylphenyl)-1-(3-pyridinyl)-2-propen-1-one (C),
2-n-butyl-3-(4fluorophenyl)-1-(3-pyridinyl)-2-propen-1-ol (A), and
2-n-butyl-3-(4methylphenyl)-1-(3-pyridinyl)-2-propen-1-ol (B)
disclosed in EP-214,566.

USE EXAMPLE 1

Action on Wheat Mildew

Leaves of pot-grown wheat seedlings of the "Frü gold" variety were sprayed with aqueous liquors containing (dry basis) 80% of active ingredient and 20% of emulsifier, and dusted, 24 hours after the sprayed-on layer had dried, with spores of wheat mildew (*Erysiphe graminis* var. *tritici*). The plants were then set up in the greenhouse at from 20° to 22° C. and a relative humidity of from 75 to 80%. The extent of mildew spread was assessed after 7 days.

The results show that active ingredients 1 and 5, when employed as 0.025 and 0.006 wt % spray liquors, had a better fungicidal action (97%) than prior art active ingredients A, B and C (70%).

USE EXAMPLE 2

Action on Cucumber Mildew

Leaves of pot-grown cucumber seedlings of the "Chinesische Schlange" variety were sprayed at the two-leaf stage with an aqueous conidial suspension of cucumber mildew. After about 20 hours, these plants were sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 70 to 80%. The extent of fungus spread was determined 21 days after inoculation.

The results show that active ingredients 1, 5 and 6, when employed as 0.0125 and 0.006 wt % spray liquors, had a better fungicidal action (90%) than prior art active ingredients A and B (10%).

USE EXAMPLE 3

Action on *Plasmopara viticola*

Leaves of potted vines of the Müer-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 1, 5 and 6, when applied as 0.05 wt % spray liquors, had a better fungicidal action (97%) than prior art comparative agents A, B and C (50%).

USE EXAMPLE 4

Action on Pyrenophora teres

Barley seedlings of the "Igri" variety were sprayed to runoff at the 2-leaf stage with aqueous suspensions containing (dry basis) 80% of active ingredient and 20% emulsifier. After 24 hours the plants were inoculated with a spore suspension of the fungus *Pyrenophora teres* and placed for 48 hours in a high-humidity climatic cabinet kept at 18° C. The plants were then cultivated for a further 5 days in the greenhouse at 20°-22° C. and a relative humidity of 70%. The extent of fungus spread was then determined.

The results show that active ingredients 1, 5 and 6, when applied as 0.5% spray liquors, had a better fungicidal action (97%) than prior art active ingredients A, B and C (50%).

We claim:

1. A 3-substituted pyridine of the formula:

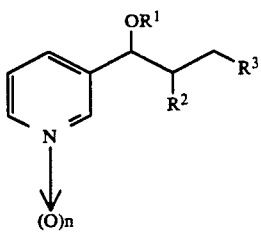

where
$R^1$ is hydrogen, $C_1$-$C_8$-alkyl, $C_3$-$C_8$-alkenyl, $C_3$-$C_8$-alkynyl, $C_2$-$C_{12}$-acyl, $C_2$-$C_{12}$-haloacyl, acryloyl, benzoyl which is unsubstituted or substituted by $C_1$-$C_4$-alkyl, $C_1$-$C_4$-alkoxy, phenyl, acetoxy, $C_1$-$C_4$-haloalkyl, halogen or nitro, or is benzyl which is unsubstituted or substituted by $C_1$-$C_4$-alkyl, $C_1$-$C_4$-alkoxy, $C_1$-$C_4$-haloalkyl, halogen, cyano or nitro;
$R_2$ is $C_1$-$C_{12}$-alkyl
$R^3$ is the radical:

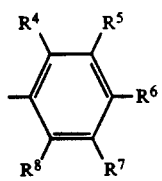

with one or two of groups $R^4$ to $R^8$ being identical or different and each selected from the group consisting of hydrogen, $C_1$-$C_4$-alkyl, $C_1$-$C_4$-alkoxy, $C_1$-$C_4$-haloalkyl, $C_2$-$C_4$-alkoxycarbonyl, phenyl, hydroxy or halogen with the remaining groups being hydrogen, or $R^4$ and $R^5$, or $R^5$ and $R^6$, denoting the group —CH=CH—CH=CH—,
n is 0 or 1,
and its plant-tolerated salts.

2. A fungicidal composition comprising an inert carrier and a fungicidally effective amount of a 3-substituted pyridine of the formula:

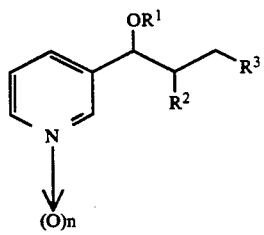

wherein
$R^1$ is hydrogen, $C_1$-$C_8$-alkyl, $C_3$-$C_8$-alkenyl, $C_3$-$C_8$-alkynyl, $C_2$-$C_{12}$-acyl, $C_2$-$C_{12}$-haloacyl, acryloyl, benzoyl which is unsubstituted or substituted by $C_1$-$C_4$-alkyl, $C_1$-$C_4$-alkoxy, phenyl, acetoxy, $C_1$-$C_4$-haloalkyl, halogen or nitro, or is benzyl which is unsubstituted or substituted by $C_1$-$C_4$-alkyl, $C_1$-$C_4$-alkoxy, $C_1$-$C_4$-haloalkyl, halogen, cyano or nitro;
$R_2$ is $C_1$-$C_{12}$-alkyl
$R^3$ is the radical:

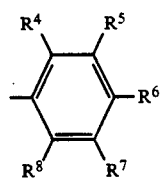

with one or two of groups $R^4$ to $R^8$ being identical or different and each selected from the group consisting of hydrogen, $C_1$-$C_4$-alkyl, $C_1$-$C_4$-alkoxy, $C_1$-$C_4$-haloalkyl, $C_2$-$C_4$-alkoxycarbonyl, phenyl, hydroxy or halogen with the remaining groups being hydrogen, or $R^4$ and $R^5$, or $R^5$ and $R^6$, denoting the group —CH=CH—CH=CH—,
n is 0 or 1,
and its plant-tolerated salts.

3. A method for combating fungi, wherein the fungi, or materials, plants, soils or seed are treated with a fungicidally effective amount of a 3-substituted pyridine of the formula:

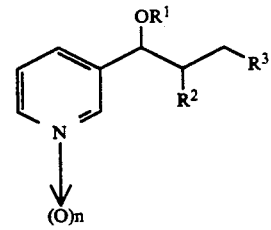

where
$R^1$ is hydrogen, $C_1$-$C_8$-alkyl, $C_3$-$C_8$-alkenyl, $C_3$-$C_8$-alkynyl, $C_2$-$C_{12}$-acyl, $C_2$-$C_{12}$-haloacyl, acryloyl, benzoyl which is unsubstituted or substituted by $C_1$-$C_4$-alkyl, $C_1$-$C_4$-alkoxy, phenyl, acetoxy, $C_1$-$C_4$-haloalkyl, halogen or nitro, or is benzyl which is unsubstituted or substituted by $C_1$-$C_4$-alkyl, $C_1$-$C_4$-alkoxy, $C_1$-$C_4$-haloalkyl, halogen, cyano or nitro;
$R_2$ is $C_1$-$C_{12}$-alkyl
$R^3$ is the radical:

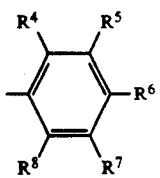

with one or two of groups $R^4$ to $R^8$ being identical or different and each selected from the group consisting of hydrogen, $C_1$–$C_4$-alkyl, $C_1$–$C_4$-alkoxy, $C_1$–$C_4$-haloalkyl, $C_2$–$C_4$-alkoxycarbonyl, phenyl, hydroxy or halogen with the remaining groups being hydrogen, or $R^4$ and $R^5$, or $R^5$ and $R^6$, denoting the group —CH=CH—CH=CH—, n is 0 or 1, and its plant-tolerated salts.

4. The 3-substituted pyridine compound of claim 1, wherein $R^1$ is hydrogen, methyl, ethyl, n-propyl, isopropyl, n-butyl, isobutyl, tert-butyl, n-pentyl, isopentyl, n-hexyl, neohexyl, n-heptyl, n-octyl, 2,4,4-trimethylpent-2-yl, 2-ethylhexyl, allyl, 2-methylallyl, 3-methylallyl, 3,3-dimethylallyl, 3-buten-1-yl, 3-octen-1-yl, propargyl, 3-octyn-1-yl, acetyl, mono-, di- or trichloroacetyl, trifluoroacetyl, propionyl, 3-bromo-propionyl, butyryl, 4-bromobutyryl, 3-methylbutyryl, 3,3-dimethylbutyryl, pentanoyl, hexanoyl, heptanoyl, octanoyl, 2-ethylhexanoyl, nonanoyl, decanoyl, lauroyl, dodecanoyl, acryloyl, benzoyl, mono-, di- or trimethylbenzoyl, 4-tert-butylbenzoyl, 4-phenylbenzoyl, fluorobenzoyl, mono-, di- or trichlorobenzoyl, trifluoromethylbenzoyl, mono-, di- or trimethoxybenzoyl, 2-acetoxybenzoyl, mono- or dinitrobenzoyl, benzyl, mono-, di- or trimethylbenzyl, 4-tert-butylbenzyl, mono-, di- or trimethoxybenzyl, trifluoromethylbenzyl, trichloromethylbenzyl, mono-, di- or trichlorobenzyl, cyanobenzyl or mono- or dinitrobenzyl.

5. A fungicidal composition according to claim 2, wherein said composition comprising from 0.1 to 95% by weight active fungicidal compound.

6. The method of claim 3, wherein from 0.02 to 3 kg of active fungicidal ingredient is applied per hectare.

7. 2-n-Butyl-3-(4-fluorophenyl)-1-(3-pyridinyl)-propan-1-ol.

* * * * *

UNITED STATES PATENT AND TRADEMARK OFFICE
CERTIFICATE OF CORRECTION

PATENT NO. : 5,192,767

DATED : March 9, 1993

INVENTOR(S) : B. Zipperer

It is certified that error appears in the above-identified patent and that said Letters Patent is hereby corrected as shown below:

On the title page, Item [63] should read as follows:
--Continuation of Ser. No. 257,278, Oct. 13, 1988, abandoned--

On the title page, Item [73], the city of the first inventor has been omitted, should read as follows:
--Bernhard Zipperer, Dirmstein;--

Signed and Sealed this

Twenty-third Day of November, 1993

Attest:

BRUCE LEHMAN

*Attesting Officer*     *Commissioner of Patents and Trademarks*